United States Patent [19]
Bond

[11] Patent Number: 4,718,634
[45] Date of Patent: Jan. 12, 1988

[54] PHYSIOLOGICAL PRESSURE MONITORING SYSTEM FLUSH VALVE

[75] Inventor: Albert K. Bond, Burlington, Mass.
[73] Assignee: Hewlett-Packard Company, Palo Alto, Calif.
[21] Appl. No.: 910,543
[22] Filed: Sep. 23, 1986
[51] Int. Cl.$^4$ .................... F16K 51/00; A61M 5/00
[52] U.S. Cl. ................................. 251/117; 251/342; 604/34
[58] Field of Search ............... 251/117, 342; 604/30, 604/34, 250

[56] References Cited

U.S. PATENT DOCUMENTS

| | | | |
|---|---|---|---|
| 3,675,891 | 7/1972 | Reynolds et al. | 251/117 |
| 4,192,303 | 3/1980 | Young et al. | 251/117 X |
| 4,267,835 | 5/1981 | Barger et al. | 251/342 X |
| 4,278,083 | 7/1981 | Young et al. | 251/117 X |
| 4,440,378 | 4/1984 | Sullivan | 604/250 X |
| 4,550,748 | 11/1985 | Nuny | 251/117 X |

Primary Examiner—Chambers A. Michael
Assistant Examiner—John C. Fox
Attorney, Agent, or Firm—Donald N. Timbie

[57] ABSTRACT

A valve assembly in which the ends of a tube having a passageway extending therethrough are respectively mounted in cavities in separate housings each of which has a passageway communicating with its cavity. An elastic sleeve is placed about the adjacent ends of the housings and a path is formed in the housings that bypasses the tube. One housing is attached to its end of the tube so as to move therewith. An actuator is connected to the housings so as to position the other end of the tube against the bottom of the cavity in the other housing. This forms a seal that prevents fluid flow in the bypass. When the actuator is squeezed, the housings are moved apart so as to open the seal and permit a fast flow of fluid through the bypass.

5 Claims, 3 Drawing Figures

PHYSIOLOGICAL PRESSURE MONITORING SYSTEM FLUSH VALVE

BACKGROUND OF THE INVENTION

In monitoring the blood pressure at a given point in the blood vessels of a patient, a catheter may be inserted through the blood vessels until one end reaches the point of interest. A slow flow of saline solution is maintained through the catheter in order to prevent it from becoming clogged by the coagulation of blood. In order to wash blood from the catheter after a blood sample is drawn through it or to shorten the time for filling the dome that couples the blood pressure to a transducer, means are provided for causing a momentary fast flow of saline solution through the catheter. As the amount of saline solution that can be safely injected into the blood stream of a patient is limited, the means must be designed so as the cut off the fast flow within a short time after the measure is deactivated. It is important that the means be free from pockets in which bubbles can gather that would deteriorate the blood pressure signals derived and that impurities be prevented from reaching the catheter.

BRIEF SUMMARY OF THE INVENTION

In accordance with this invention, two housings are provided, each having a cavity in one end that communicates with a passageway in the other. The slow flow is provided by a passageway extending through a tube having its ends respectively mounted in the cavities so that the passageways are in communication. One housing is provided with means for gripping its end of the tube so that the two move together. The adjacent surfaces of the other end of the tube and the cavity of the other housing are such as to form a seal when they are in contact. Means are provided for defining a path in the housing between the passageways in the housings so as to provide a bypass around the tube through which a fast flow of fluid can occur when the seal referred to is opened. Resilient means are provided for urging the housings toward each other so as to form the seal and prevent fluid from flowing in the bypass path when the means is not activated and for pulling the housings apart so as to open the seal and permit flow through the bypass path when activated.

BRIEF DESCRIPTION OF THE DRAWINGS

FIG. 1A is a cross section of tube T taken at AA of FIG. 1.

DETAILED DESCRIPTION OF THE INVENTION

Figure 1:
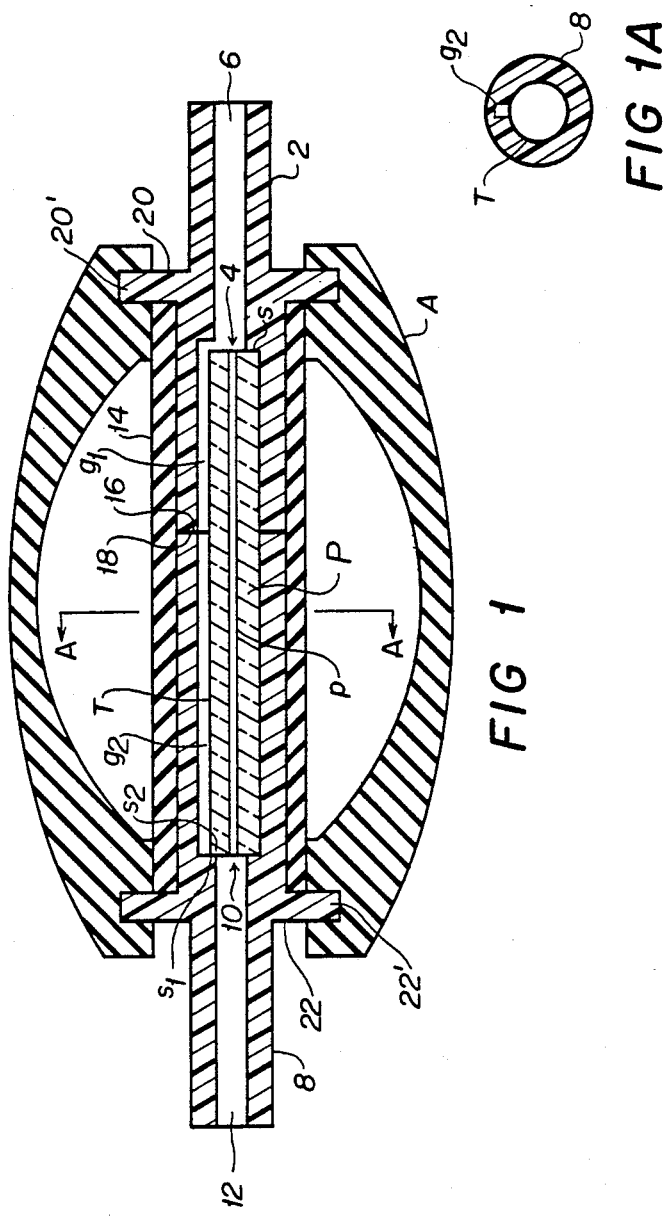
FIG. 1 is a cross section view of the valve assembly of the invention taken through the axis of the tube and showing the portion of the parts during a fast flow.

FIG. 1 shows the relative positions of the various parts that are required to produce a slow flow of blood. A housing 2 has a cavity 4 at one end that communicates with a passageway 6 at the other end, and a housing 8 has a cavity 10 at one end that communicates with a passageway 12 at the other end. A tube T that is preferably made of stiff material such as glass has a small bore passageway p extending therethrough that communicates with the passageways 6 and 12. The end of the tube T within the cavity 4 is attached to the housing 2 so as to move with it. This could be effected by use of an adhesive but it is preferable that the cavity 4 fit tightly around the Tube T so as to grip it. When, as in FIG. 1, the surface $s_1$ at the other end of the tube T is in contact with the surface $s_2$ at the bottom of the cavity 10 in the housing 8, a seal is formed so that fluid cannot pass radially outward but is confined to flowing in the passageway 12, the passageway p, the tube T and the passageway 6.

A sleeve 14 of elastic material is mounted about the adjacent ends of the housings so as to respectively form seals therewith and prevent fluid from escaping from between the adjacent ends 16 and 18 of the housings 2 and 8 respectively. In this particular embodiment, the sleeve 14 extends from an annular ridge 20 on the housing 2 to an annular ridge 22 on the housing 8, but it could be much shorter.

An ellipsoid A made of flexible material is coupled to the housings 2 and 8 by annular grooves 20' and 22' that respectively fit over the anular ridges 20 and 22. When the ellipsoid A is in a relaxed state, the surfaces $s_1$ and $s_2$ are in contact so as to form the seal referred to. In order not to form a pocket in which bubbles can be trapped, it is preferable that the adjacent ends 16 and 18 of the housings 2 and 8 respectively be in contact.

Figure 2:
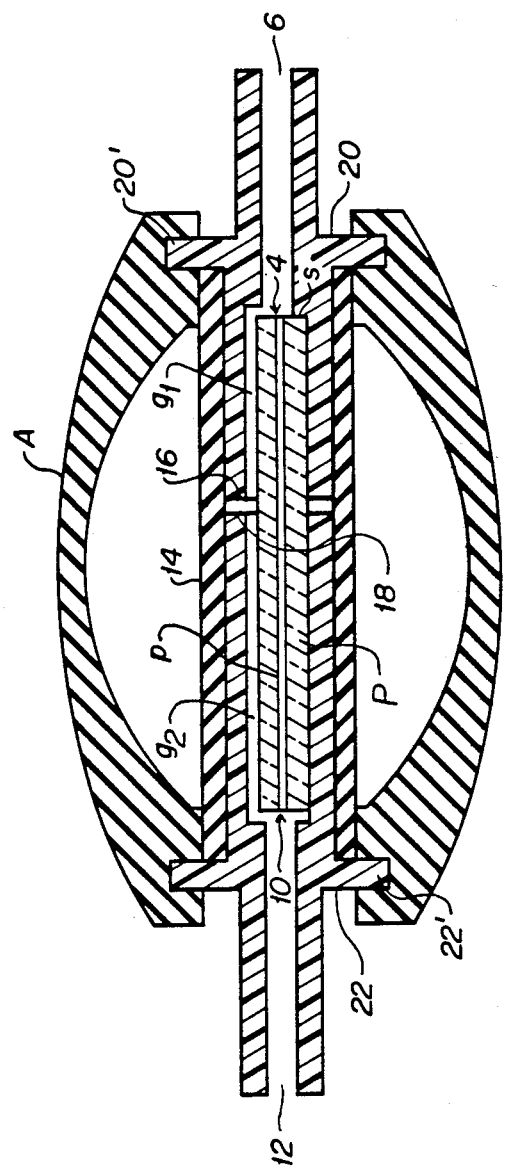
FIG. 2 is similar to FIG. 1 except that it shows the position of the parts during a slow flow.

FIG. 2 shows the relative position of the same parts that is required to produce a fast flow. In addition, means are provided for forming a pathway that forms a bypass around the tube T. In this particular embodiment this is accomplished by a groove $g_1$ in the inner surface of the cavity 4 that extends from the open end to the closed end of the cavity and a groove $g_2$ in the inner surface of the cavity 10 that extends from the open end to the closed end of the cavity. FIG. 1A shows a cross section of tube T taken at AA of FIG. 1 so as to illustrate the groove $g_2$, but $g_1$ would be the same. A shoulder s that is at a given point in the bottom of the cavity 4 prevents the end of the tube T from contacting the bottom cavity in order to permit fluid flow from $g_1$ to the passageway 6.

In order to attain fast fluid flow, the ellipsoid A is squeezed in a radially inward direction so as to slightly increase its length and pull the housing 2 and the tube T into the position shown wherein the seal between the surfaces $s_1$ and $s_2$ is opened so as to permit fluid flow from the passageway 12 to the passageway 6 via the grooves $g_1$ and $g_2$. The fast flow continues as long as the actuator A is squeezed, but as soon as it is released, it shortens so as to return to the position of FIG. 1 for slow flow. Note that the gap that appears between the surfaces 16 and 18 in FIG. 2 is greatly reduced. If any gap remained, it could act as a trap for bubbles.

Whereas the actuator A has been shown as being generally ellipsoidal, this precise shape is not required. Many other shapes could be used. Such shapes are meant to be covered by the term ellipsoid used in the claims.

What is claimed is:

1. A valve assembly comprising:
    a first housing having a cavity in one end and a passageway in the other end that communicates with said cavity;
    a second housing having a cavity in one end and a passageway in the other end that communicates with the latter cavity;
    a tube having ends and a passageway extending therethrough between said ends, the ends of said tube being respectively mounted in said cavities so as to place the passageway of said tube in communication with the passageways in said housings;

means for coupling the end of said tube in the cavity of said first housing to said first housing so that they will move together;

an elastic sleeve coaxial with said tube and outside of it, said sleeve having ends respectively coupled to said housings so as to respectively form seals therewith;

means defining a path in said housings in parallel with the passageway in said tube;

means for providing communication between the passageway in said first housing and the adjacent end of the path within it;

the adjacent surfaces of the cavity in the second housing and the end of the tube therein normally being in contact so as to form a seal that prevents communication between the passageway in said second housing and the path in said second housing; and resilient means coupled to said housings that permits said adjacent surfaces to be in contact when not activated and for separating said housing and said adjacent surfaces when activated.

2. A valve assembly as set forth in claim 1 wherein
said means defining paths in said housings are grooves in the walls of the cavities; and
said resilient means is comprised of an ellipsoid having the housings and tube mounted within it between its smaller ends, the ends being respectively attached to said housings.

3. A valve assembly as set forth in claim 2 wherein a shoulder is provided at the bottom of the cavity in said first housing so as to provide space between the end of the tube and the housing through which fluid can flow in passing from the groove to the passageway in said first housing.

4. A valve assembly as set forth in claim 2 wherein said housings are in contact when said ellipsoid is in a relaxed state.

5. A valve assembly as set forth in claim 2 wherein said adjacent surfaces are in contact when said ellipsoid is in a relaxed state and wherein said adjacent surfaces are spaced from each other when actuation forces are applied to said ellipsoid in a radial direction that is toward said tube.

* * * * *